US00PP36978P2

(12) United States Plant Patent
Yencho et al.

(10) Patent No.: US PP36,978 P2
(45) Date of Patent: Sep. 23, 2025

(54) SWEETPOTATO PLANT NAMED 'NCORNSP-033SCMP'

(50) Latin Name: *Ipomoea batatas*
Varietal Denomination: NCORNSP-033SCMP

(71) Applicant: North Carolina State University, Raleigh, NC (US)

(72) Inventors: George Craig Yencho, Raleigh, NC (US); Kenneth Vincent Pecota, Raleigh, NC (US); Christopher Heim, Morrisville, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/093,526

(22) Filed: Mar. 28, 2025

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP21,743 P2 * 3/2011 Yencho ..... A01H 6/00 Plt./373

* cited by examiner

*Primary Examiner* — Susan McCormick Ewoldt
(74) *Attorney, Agent, or Firm* — Myers Bigel, P.A.

(57) ABSTRACT

'NCORNSP-033SCMP' is a compact, non-twining, semi-upright variety producing many short shoots. It is distinguishable from other cultivars by its palmate, deeply lobed leaves with 7-9 lobes, a compact habit, and semi-erect mounding plant architecture. The purple leaves, deep-lobing, quantity of lobes, short internodes, and the plant architecture distinguishes 'NCORNSP-033SCMP' amongst the current ornamental sweetpotatoes in the marketplace. 'NCORNSP-033SCMP' also exhibits good vigor and is very well branched, a growth habit that promotes good plant production in the greenhouse for wholesale distributors. In greenhouse and field trials, 'NCORNSP-033SCMP' has been shown to be suitable for use as a landscape or containerized plant.

5 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-033SCMP'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast-growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they often do not produce attractive, enlarged storage roots suitable for human consumption. Instead, they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g., pale yellow to dark purple with some exhibiting temporal and individual leaf color variegation patterns) and plant shapes (e.g., mounded and very compact to prostrate and highly spreading). They can be grown in a potted plant and/or mixed planting format, and they can cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out-compete other species in mixed containers.

'NCORNSP-033SCMP' was bred to meet the increasing demand for new ornamental sweetpotatoes. 'NCORNSP-033SCMP' is a compact, non-twining, semi-upright variety producing many short shoots. It is distinguishable from other cultivars by its palmate, deeply lobed leaves with 5-9 lobes, a compact habit, and semi-erect mounding plant architecture. The purple leaves, short internodes, and the plant architecture, which promotes good plant production in the greenhouse for wholesale distributors, distinguishes 'NCORNSP-033SCMP' amongst the current ornamental sweetpotatoes in the marketplace. 'NCORNSP-033SCMP' exhibits very good vigor and is very well branched. In greenhouse and field trials conducted since 2022 by the breeding program and industry collaborators, 'NCORNSP-033SCMP' has been shown to be of similar vigor to *Ipomoea batatas* 'NCORNSP-027SCMG' (U.S. Plant Pat. No. 34,146) and 'NC3147-018ORN' (U.S. Plant Pat. No. 21,743) and is suitable for use as a landscape or containerized plant. 'NCORNSP-033SCMP' has not been observed to produce flowers under short-or long-day conditions.

Lineage. 'NCORNSP-033SCMP' (breeding designation NC10565-001ORN or MD10565-001) originated from hand-pollinated seed from the proprietary *Ipomoea batatas* breeding lines NC8823-031ORN (the female parent; not patented) and NC9609-007ORN (the male parent; not patented). Botanical seed was harvested from ornamental lines grafted onto a flower-inducing *Ipomoea setosa* sweetpotato line in greenhouses between October 2021 and April 2022 in Raleigh, North Carolina. NC8823-031ORN resulted from open-pollinated seed harvested from the proprietary *Ipomoea batatas* breeding line NC8107-003ORN (the female parent; not patented). NC9609-007ORN resulted from hand-pollinated seed collected from NC8924-009ORN (the female parent; not patented) and NC8939-001ORN (the male parent; not patented). Botanical seed from this family were planted in the greenhouse in December 2021. The first cycle of selection on the population was exercised at the seedling tray stage and survivors were transferred to a single 6-inch pot, which was then maintained in the greenhouse. Cuttings (2 each) were taken from the plants in April and planted in the field as unreplicated 2-plant plots, during mid-June 2022. The single, individual plant now known as 'NCORNSP-033SCMP' was selected in September 2022 because of its combination of exceptional features, and it has been propagated asexually since that time.

Asexual Reproduction. Since its selection, *Ipomoea batatas* 'NCORNSP-033SCMP' has been asexually reproduced in Raleigh, North Carolina predominantly by vegetative propagation of vine cuttings. Successively, there have been six cycles of vegetative propagation, one cycle of tissue culture micropropagation, and multiple vegetative propagation cycles to increase plant numbers. Asexual reproduction of 'NCORNSP-033SCMP' by cuttings has shown that the unique features of the new cultivar are stable, and the plant reproduces true to type in successive generations.

SUMMARY OF THE INVENTION

'NCORNSP-033SCMP' is a compact, non-twining, semi-upright variety producing many short shoots. It is distinguishable from other cultivars by its palmate, deeply lobed leaves with 5-9 lobes, a compact habit, and semi-erect mounding plant architecture. The purple leaves, deep lobing, quantity of lobes, short internodes, and the plant architecture distinguishes 'NCORNSP-033SCMP' amongst the current ornamental sweetpotatoes in the marketplace. 'NCORNSP-033SCMP' also exhibits good vigor and is very well branched, a growth habit that promotes good plant production in the greenhouse for wholesale distributors. In greenhouse and field trials conducted since 2022 by the breeding program and industry collaborators, 'NCORNSP-033SCMP' has been shown to be similar in vigor and leaf form to *Ipomoea batatas* 'NCORNSP-027SCMG' and is suitable for use as a landscape or containerized plant. 'NCORNSP-033SCMP' has not been observed to produce flowers under short-or long-day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Ipomoea batatas*.

DETAILED BOTANICAL DESCRIPTION OF THE NEW VARIETY

The following is a detailed description of the botanical characteristics of a new and distinct cultivar of *Ipomoea batatas* plant known by the cultivar name 'NCORNSP-033SCMP'. All colors cited herein refer to The Royal Horticulture Society Colour Chart designations (The Royal Horticultural Society, London, 2001, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions reported herein are from a group of 73-day-old specimens grown individually in six-inch azalea pots. The plants were grown in Raleigh, North Carolina, under commercial practice in a glass-covered greenhouse, where, during the fall, day and night temperatures range between 30-40° C. and 22-26° C., respectively. After rooting, plants were treated with 200 ppm 20-10-20 fertilizer weekly. Plant measurements were taken in September 2024 at the Horticulture Field Lab (HFL) in Raleigh, North Carolina. *Ipomoea batatas* 'NCORNSP-033SCMP' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Ipomoea batatas* (L.) Lam.

*Common name.*—Ornamental Sweetpotato.

*Variety name.*—'NCORNSP-033SCMP'.

Growth conditions: *Ipomoea batatas* 'NCORNSP-033SCMP' has very good vigor and a moderate growth rate. In locations with mild winter conditions, *Ipomoea batatas* 'NCORNSP-033SCMP' will grow perennially; otherwise, it is an annual plant. Like other cultivated sweetpotatoes, wind or rain rarely causes much damage to 'NCORNSP-033SCMP', but if damage does occur, the plant drops the damaged leaves and grows new shoots at nodes where the leaves were lost. Under low light levels in a greenhouse, 'NCORNSP-033SCMP' can develop intumescence, which will remain on the affected foliage, but will be outgrown with new foliage.

Figure 1A:
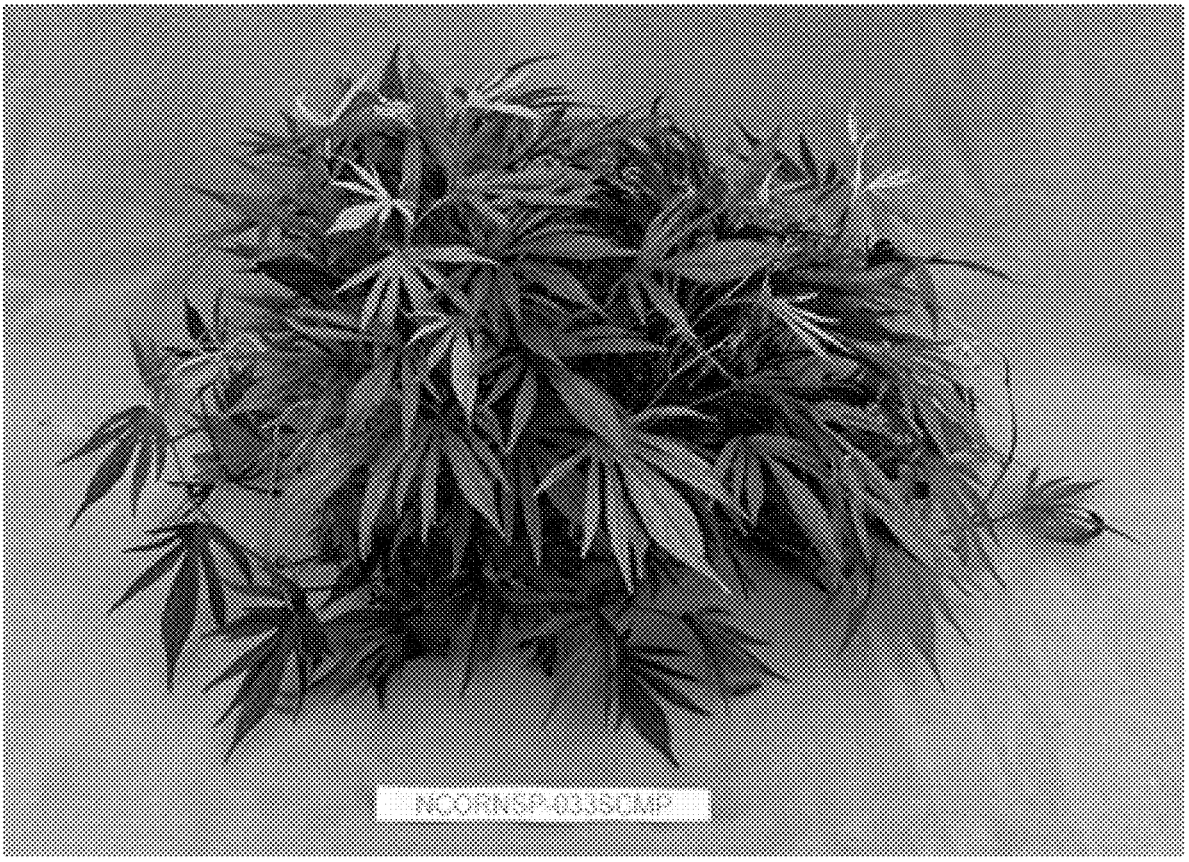
FIGS. 1A-1B are color photographs of a typical specimen of greenhouse grown *Ipomoea batatas* 'NCORNSP-033SCMP' in a 6-inch pot from the side (FIG. 1A) and top (FIG. 1B), 74 days after planting.
Figure 1B:
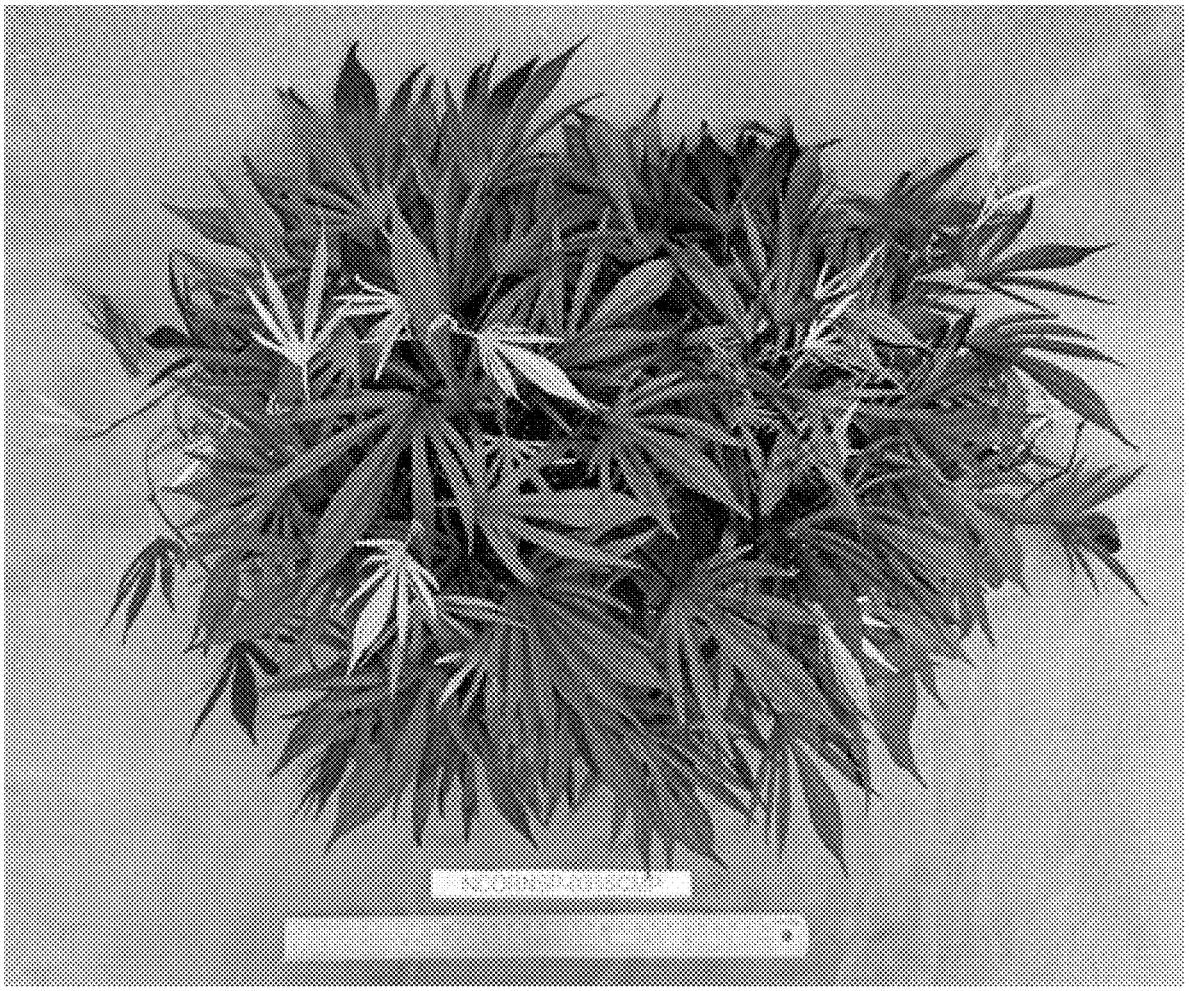
Figure 2A:
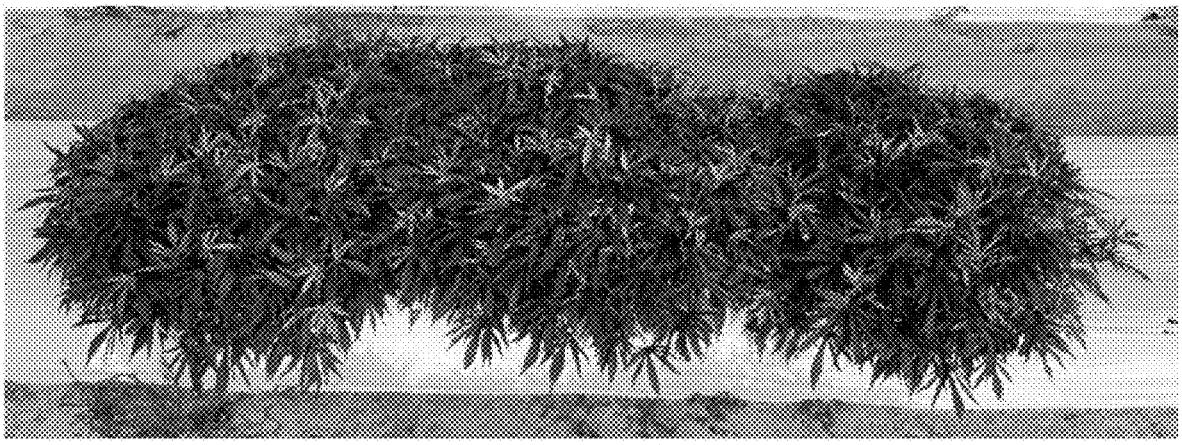
FIGS. 2A-2B are color photographs of a typical specimen of *Ipomoea batatas* 'NCORNSP-033SCMP' from side (FIG. 2A) and top (FIG. 2B) in the field, 79 days after planting.
Figure 2B:
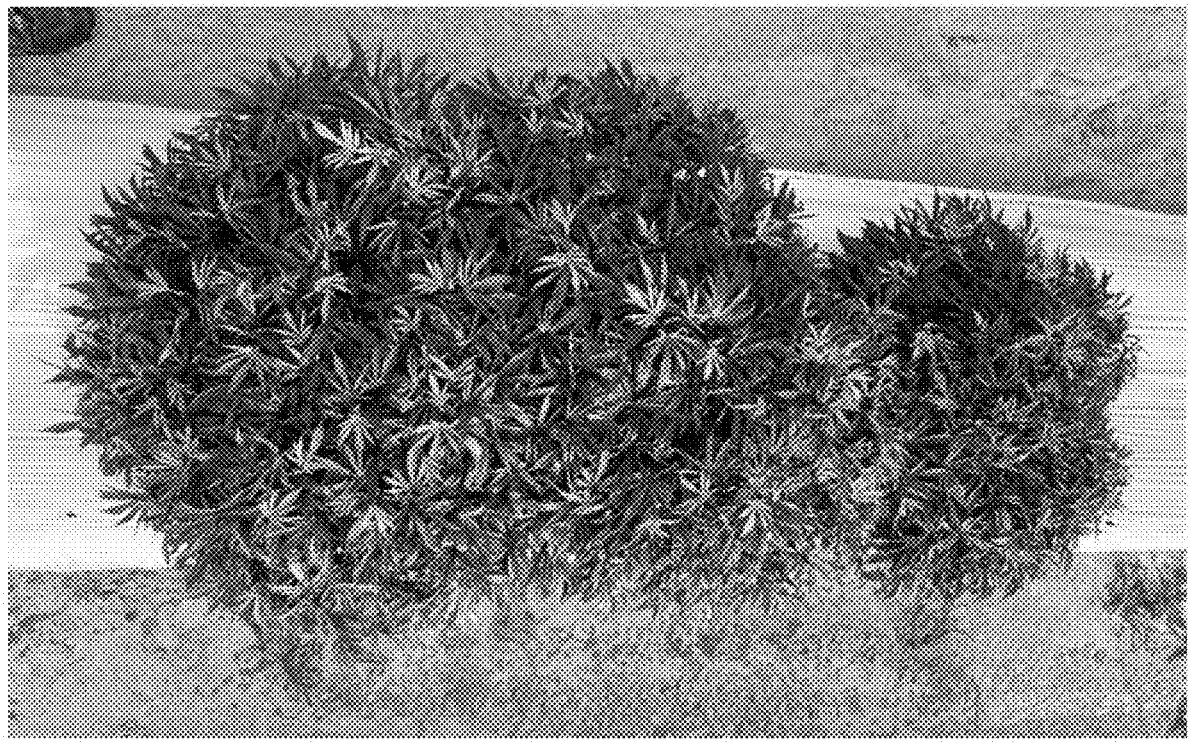
Figure 3A:
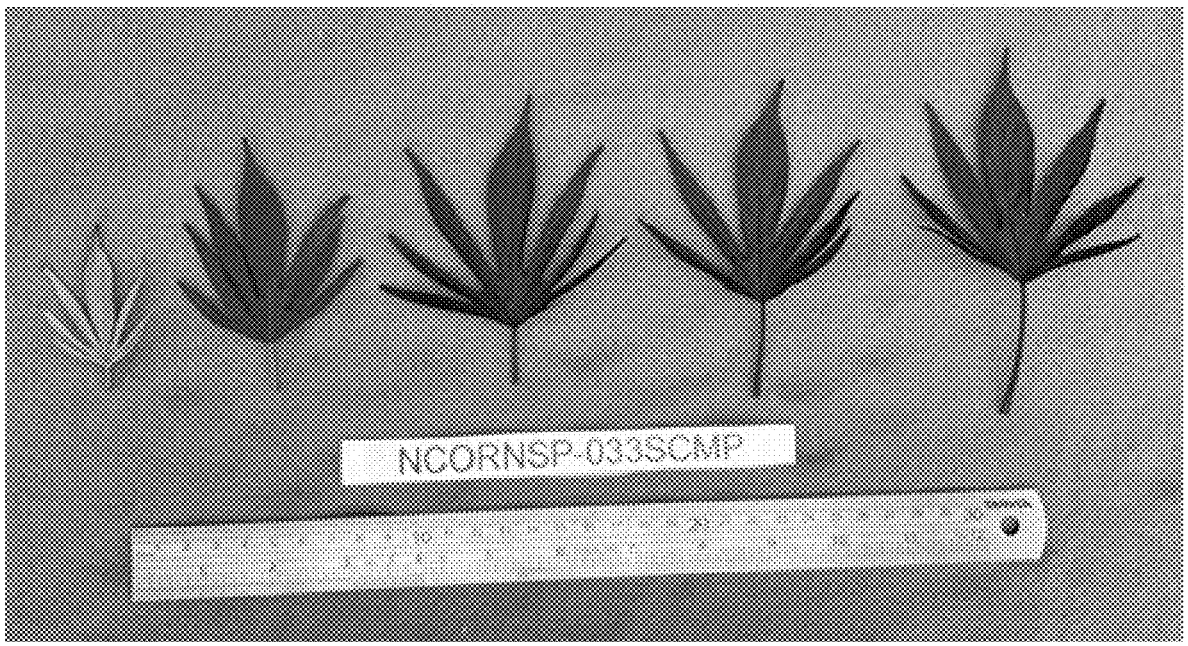
FIGS. 3A-3B are color photographs showing the upper (FIG. 3A) and lower (FIG. 3B) surfaces of mature leaves produced by *Ipomoea batatas* 'NCORNSP-033SCMP' 74 days after planting.
Figure 3B:
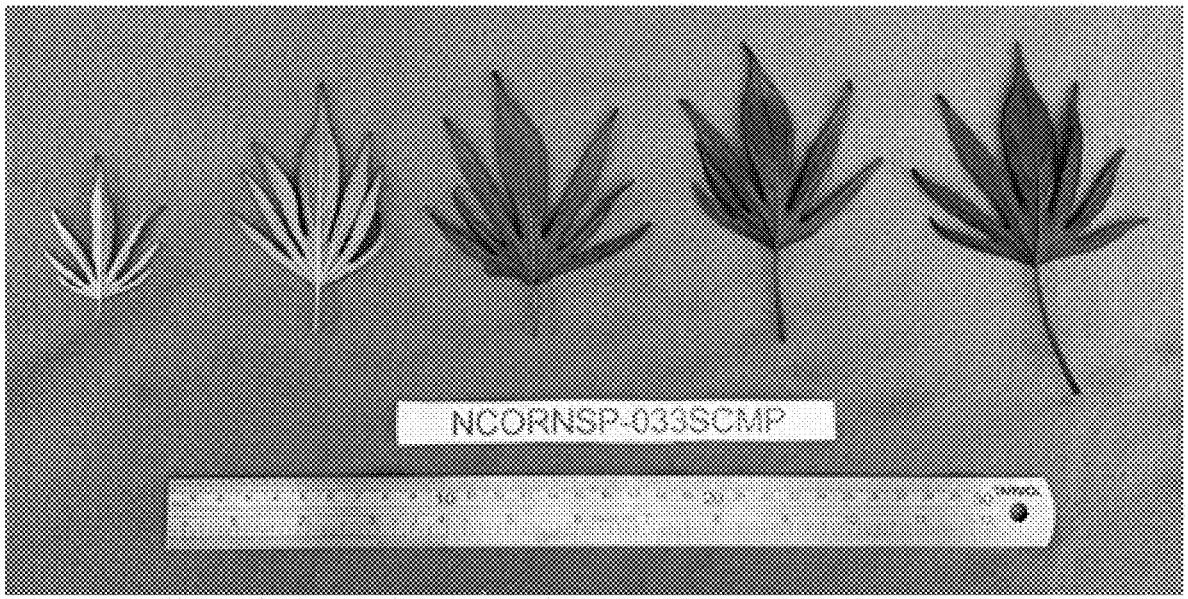
Figure 4A:
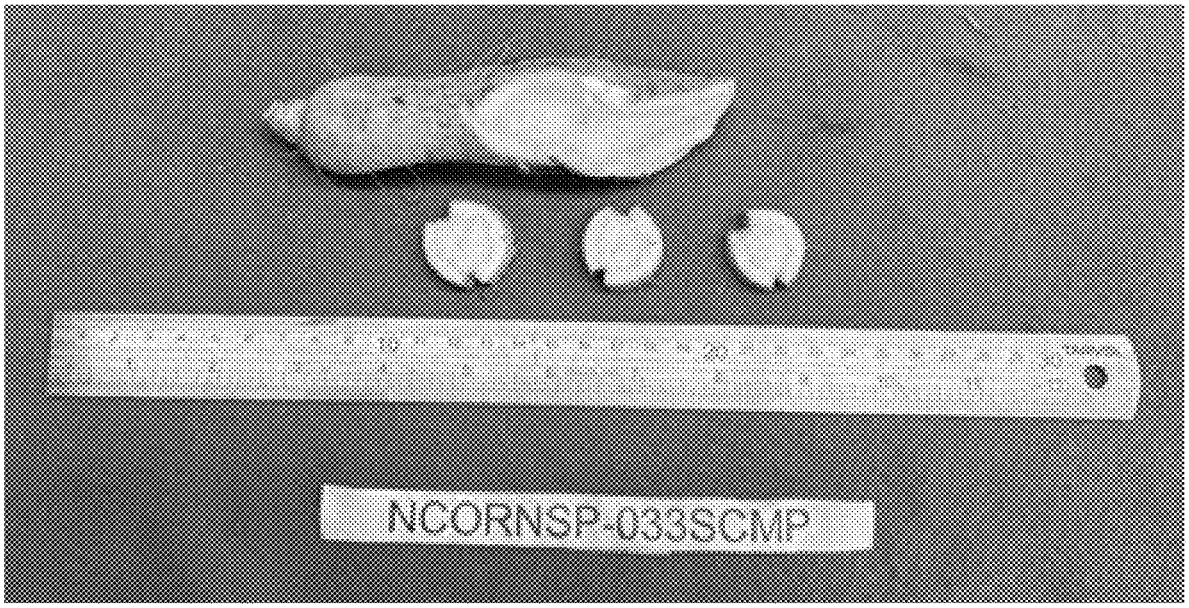
FIGS. 4A-4B are color photographs showing storage roots produced by *Ipomoea batatas* 'NCORNSP-033SCMP' in the field, 126 days after planting.
Figure 4B:
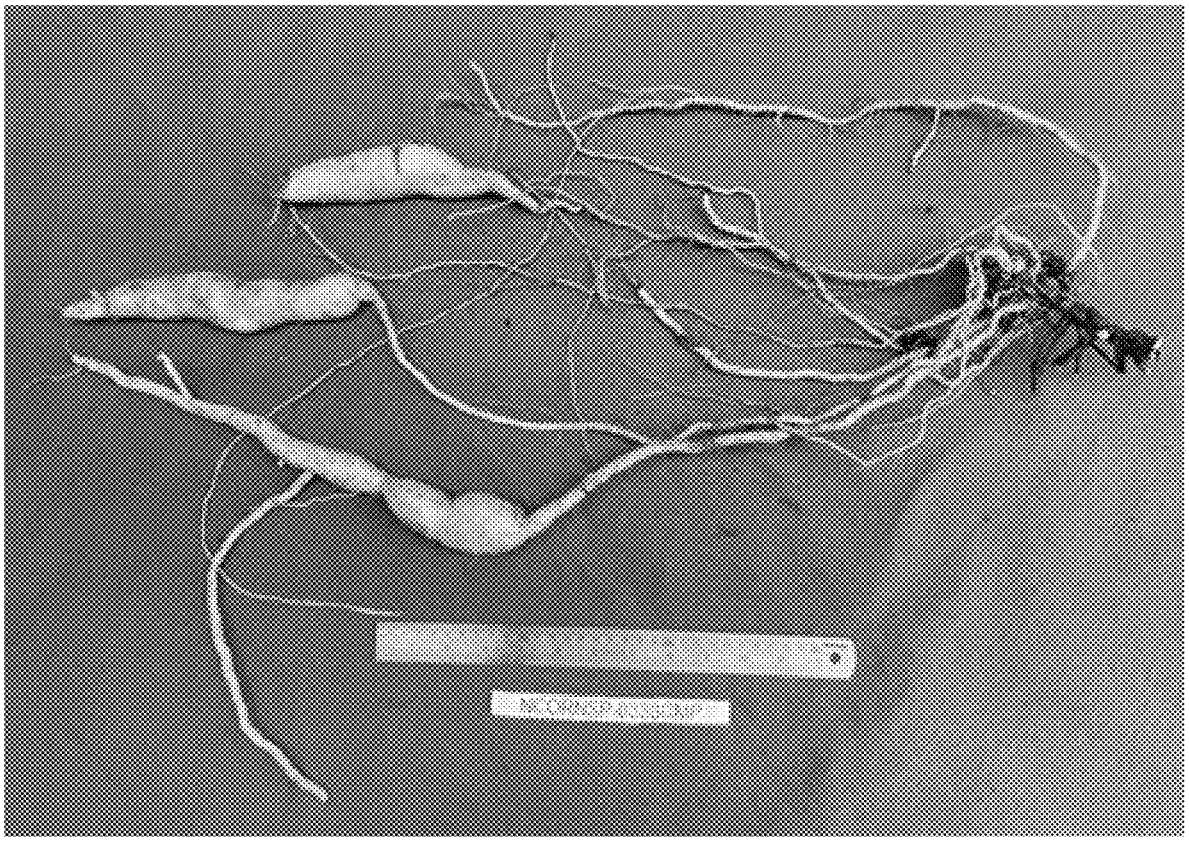

Aboveground structure and coloration: FIGS. 1A, 1B, 2A, 2B, 3A and 3B show the shape and coloration of a typical specimen of *Ipomoea batatas* 'NCORNSP-033SCMP'. Color may vary somewhat due to temperature and nutrient stress. Overall, this cultivar is a compact, non-twining, semi-upright herbaceous plant that has an average height of 22.7±6.2 cm and an average area spread of 86.5±18.4 cm at 73 days after planting (DAP). The growth habit of this plant is to grow semi-upright with shoots growing upward and outward.

Branches:

*Branching habit*.—Freely-branching with about 10 primary lateral branches coming off the stem. Very dense foliage and no pinching is required to stimulate branching. Branch texture is smooth and glabrous with slight pubescence.

*Vegetative lateral branching*.—Length: 38.0±10.6 cm. Diameter: 0.23±0.04 cm. Internodes have an average length of 4.3±1.9 cm.

*Secondary lateral shoots*.—No measurable secondary lateral shoots formed on the rated plants.

*Stem*.—Round and smooth with an upward, very strong, slightly flexible, non-brittle strength. Color: Red-Purple (RHS 59A).

*Adventitious roots*.—Yellow-white (RHS 158D).

Foliage: Leaves are alternate and tend to slightly spiral around the stem. They are simple and heavily divided into 7-9 lobes. Leaf shape and size are somewhat variable. (see FIGS. 3A-3B).

*Quantity*.—Average foliage count about 14.75±2.6 leaves per lateral branch.

*Mature leaf length*.—9.8±0.6 cm.

*Mature leaf width*.—9.6±0.7 cm.

*Leaf margin*.—Entire.

*Leaf apex*.—Acuminate.

*Leaf base*.—Rounded to truncate.

*Leaf texture*.—Glabrous texture and matte finish.

*Venation*.—Palmate. Texture: Glabrous.

*Color*.—Mature leaves are greyed-purple (RHS N186A) and typically range in color within RHS 186A to 186B and 187A. See also Table 1.

*Petiole*.—Petioles are held slightly upward and curve outward. Leaf petiole has a smooth glabrous texture. Length: 9.4±3.5 cm. Diameter: 0.2±0.009 cm. Color: Red-purple (RHS 59B).

TABLE 1

Leaf color of *Ipomoea batatas*, 'NCORNSP-033SCMP'.

| Leaf Structure | Adaxial Surface | Abaxial Surface |
|---|---|---|
| Mature Leaf | Greyed-Purple (RHS N186A) | Greyed-Purple (RHS N186C) |

TABLE 1-continued

Leaf color of *Ipomoea batatas*, 'NCORNSP-033SCMP'.

| Leaf Structure | Adaxial Surface | Abaxial Surface |
|---|---|---|
| Young Leaf | Green (RHS 137C) | Green (RHS 138B) |
| Vein-mature leaf | Greyed-Purple (RHS N186A) | Greyed-Purple (RHS N186D) |
| Vein-young leaf | Green (RHS 144A) | Yellow-Green (RHS 146C) |

Inflorescence: The production of flowers by 'NCORNSP-033SCMP' is very sporadic under short day conditions and we have not been able to obtain flowers for the measurement of flower traits.

Storage root coloration: 'NCORNSP-033SCMP' plants form no, to small, underground storage roots that are typically malformed and do not meet USDA Sweetpotato Storage Root Grade Standards (see FIGS. 5A-5B). Fibrous roots are typically yellow-white (RHS 158B).

Disease or pest resistance. 'NCORNSP-033SCMP' is susceptible to whiteflies and thrips in a greenhouse environment. 'NCORNSP-033SCMP' is susceptible to damage by Japanese beetles under outdoor conditions. Its resistance or susceptibility to other known insects and pathogens of sweetpotato are unknown. Under low light conditions, slight edema may occur.

COMPARISON WITH OTHER *IPOMOEA BATATAS* CULTIVARS

'NCORNSP-033SCMP' is distinct based on leaf shape, plant architecture, and/or color. Of the common cultivars of ornamental sweetpotatoes, 'NCORNSP-033SCMP' is best compared with the 'NCORNSP-027SCMG' (U.S. Plant Pat. No. 34,146) and 'NCORNSP-011MNLC' (U.S. Plant Pat. No. 21,743) cultivars (Table 2). Like both 'NCORNSP-027SCMG' and 'NCORNSP-011MNLC', 'NCORNSP-033SCMP' has deeply lobed leaves. However, the leaf lobes of 'NCORNSP-033SCMP' are shallower than 'NCORNSP-011MNLC', and similar to 'NCORNSP-027SCMG'. 'NCORNSP-033SCMP', while similar to 'NCORNSP-027SCMG', differs in its purple foliage and stem color. 'NCORNSP-033SCMP' has more lobes per leaf than 'NCORNSP-011MNLC'. The lobes of 'NCORNSP-033SCMP' are largely linear in shape, similar to 'NCORNSP-027SCMG', whereas the lobes of 'NCORNSP-011MNLC' are narrowly oblanceolate. The habit of 'NCORNSP-033SCMP' is more compact than 'NCORNSP-011MNLC' but similar in compactness to 'NCORNSP-027SCMG'.

'NCORNSP-033SCMP' is distinct from its parents, 'NC8823-031ORN' and 'NC9609-007ORN', by its leaf lobing and structure. 'NCORNSP-033SCMP' has regular, deep lobes compared to both parents and contains narrower lobes than 'NC8823-031ORN'. The color of 'NCORNSP-033SCMP' is darker than either parent and 'NCORNSP-033SCMP' is more compact in plant habit than either parent.

TABLE 2

Comparison of 'NCORNSP-027SCMG' with other *Ipomoea batatas* cultivars.

| Characteristic | 'NCORNSP-033SCMP' | 'NCORNSP-027SCMG' (U.S. Plant Pat. No. 34,146) | 'NCORNSP-011MNLC' (U.S. Plant Pat. No. 21,743) |
|---|---|---|---|
| Plant Habit | Compact, semi-upright and mounding habit | Compact, semi-upright and mounding habit | Compact, semi-upright |
| Average Leaf Length and Width | Length: 9.8 cm Width: 9.6 cm | Length: 12.4 cm Width: 13.8 cm | Length: 11.4 cm Width: 13.8 cm |
| Foliage Color | Greyed-Purple (RHS N186A) | Yellow-Green (RHS 144B) | Greyed-Purple (RHS N186A) |
| Leaf Shape | Deeply lobed, 7-9 lobes. Entire with an acuminate apex and a lobed base. | Deeply lobed, 7-9 lobes. Entire with an acuminate apex and a lobed base. | Very deeply lobed, 5-7 lobes. Entire with oblanceolate lobes. |

We claim:

1. A new and distinct cultivar of *Ipomoea batatas* plant named 'NCORNSP-033SCMP', substantially as illustrated and described herein.

* * * * *